United States Patent [19]

Byrd

[11] 3,982,438

[45] Sept. 28, 1976

[54] MULTIPLE SAMPLE PIPETTING APPARATUS

[75] Inventor: William J. Byrd, Solana Beach, Calif.

[73] Assignee: The Salk Institute for Biological Studies, San Diego, Calif.

[22] Filed: June 23, 1975

[21] Appl. No.: 589,023

[52] U.S. Cl. .............................................. 73/425.6
[51] Int. Cl.$^2$ ............................................ B01L 3/02
[58] Field of Search ................... 73/425.4 P, 425.6; 222/263; 141/25, 26, 27

[56] References Cited
UNITED STATES PATENTS

| | | | |
|---|---|---|---|
| 3,302,462 | 2/1967 | Pursell | 73/425.6 |
| 3,568,735 | 3/1971 | Lancaster | 222/263 |
| 3,572,552 | 3/1971 | Guinn | 73/425.6 |
| 3,807,235 | 4/1974 | Lefkovitz | 73/425.6 |

*Primary Examiner*—S. Clement Swisher
*Attorney, Agent, or Firm*—Fitch, Even, Tabin & Luedeka

[57] ABSTRACT

A Multiple Sample Pipetting Device is disclosed which is adapted to remove small predetermined volumes of liquid from a plurality of sample wells arranged in a compact rectilinear array, or conversely to transfer small predetermined volumes of liquid from one large reservoir container to a plurality of sample wells arranged in the same array. The apparatus has a plurality of small tubes extending downwardly with the upper end portion communicating with reservoirs that have a predetermined volume. A flexible diaphragm extends across all of the reservoirs, and the upper ends thereof are in communication with a common manifold chamber. The application of positive or negative pressure moves the diaphragm downwardly and upwardly into contact with the lower and upper reservoir walls, respectively, and either extracts or expels liquid from the tubes. The manifold and tube holding portion of the apparatus is vertically movable so that the tubes can be lowered into the appropriate container to extract the predetermined volume of liquid material.

16 Claims, 5 Drawing Figures

MULTIPLE SAMPLE PIPETTING APPARATUS

This invention generally relates to pipetting devices which are used in microbiological, immunological and medical laboratory research.

While pipetting devices and apparatus that are adapted to simultaneously withdraw a relatively large number of samples from individual wells of liquid samples are well known, many priority devices are adapted to simultaneously extract a relatively low number, i.e., a dozen or so samples in precise predetermined quantities within the range of about 25 to about 50 microliters, other devices drop size for metering which will extract a large number of samples, i.e., 96 separate samples, typically have a volume capacity of only a few microliters, particularly when the size of the array or matrix of the total samples is relatively small. For those types of apparatus that have a flexible diaphragm that conforms to the shape of a recess when vacuum pressure is applied for the purpose of suctioning a predetermined amount of liquid up into the suction tubes, the extremely confined and highly dense array may preclude the mere enlarging of the recesses for the purpose of increasing the volume of the extracted liquid, because the enlargement may cause an overlap of the recesses with adjacent recesses.

Accordingly, it is an object of the present invention to provide an improved pipetting apparatus that is adapted to suction relatively large sample volumes considering the high density of the samples in the array.

Other objects and advantages will become apparent upon reading the following detailed description, in conjunction with the attached drawings, in which.

Figure 1:
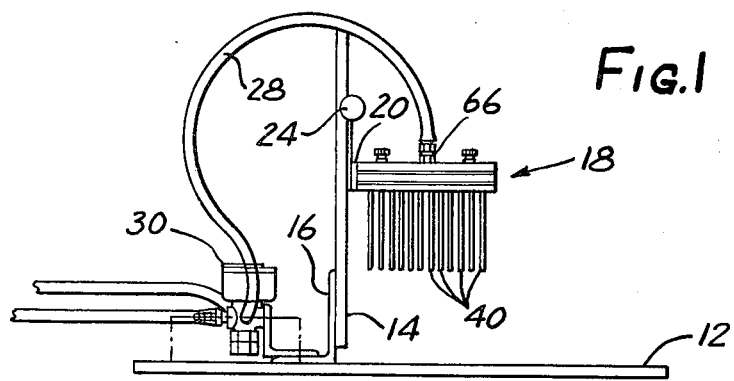
FIG. 1 is a side elevation of apparatus embodying the present invention.

Turning now to the drawings, and particularly FIG. 1, there is shown apparatus 10, embodying the present invention which includes a support base 12, a vertical frame channel member 14 which is secured to the base 12 by an angle bracket 16 or the like. A plate assembly, indicated generally at 18, is attached to a cross member 20 that is movable vertically in the channel 14. The cross member is adjustable by a rotatable knob 24 that is connected to a pinion gear (not shown) that rides in a rack (not shown) within the channel 14. The rack and pinion gear arrangement enables the cross member 20 and plate assembly 18 to be raised and lowered to the desired elevation as is necessary to extract and deposit liquid samples. The plate assembly 18 has a flexible tube 28 connected thereto, with its opposite end connected to a valve means 30 which is shown to be a two-way solenoid valve that is actuated by an electrical switch 32. The solenoid valve has a common nozzle 34 to which the flexible tube 28 is connected and alternatively communicates the common nozzle 34 with nozzles 36 and 38 which are adapted to be connected to sources of vacuum and positive pressure, respectively. The plate assembly 18 has a plurality of collector tubes 40 extending downwardly from the underside thereof for insertion into wells from which samples are to be taken. The tubes 40 are preferably about three inches long and fabricated from stainless steel.

Figure 2:
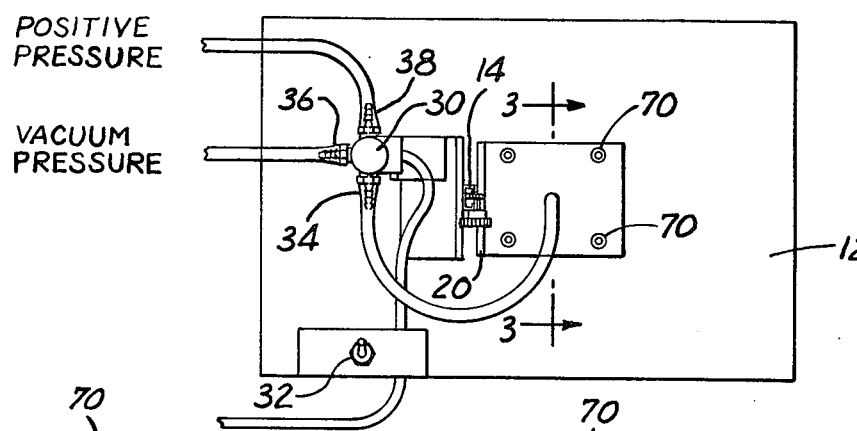
FIG. 2 is a top view of the apparatus shown in FIG. 1.
Figure 3:
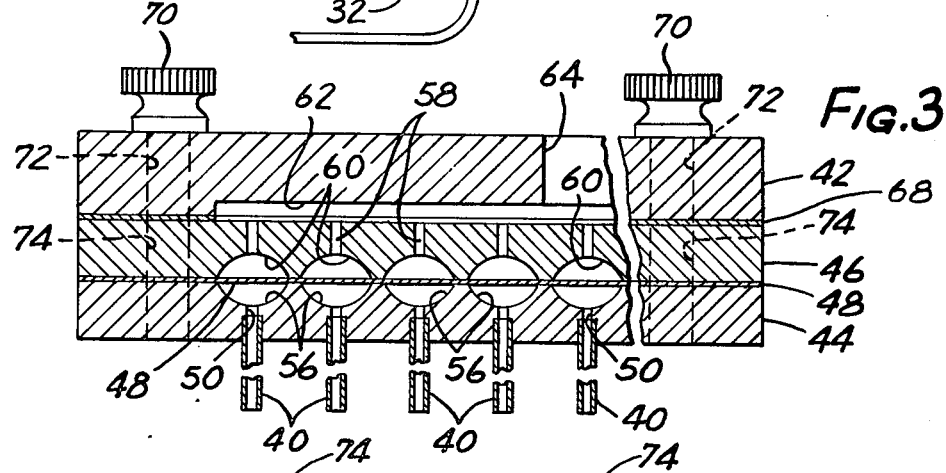
FIG. 3 is a cross sectional view, with portions removed, taken generally along the line 3—3 in FIG. 2.
Figure 4:
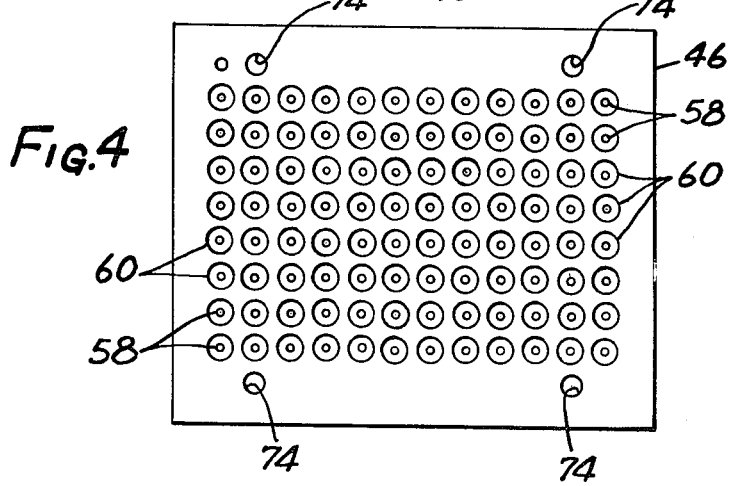
FIG. 4 is a bottom plan view of the intermediate plate of the apparatus shown in FIG. 1 and particularly illustrating the array or matrix of openings therein; and, FIG. 5 is an enlarged cross section of a portion of the collector plate illustrating the attachment of a typical collector tube to the collector plate.
Figure 5:
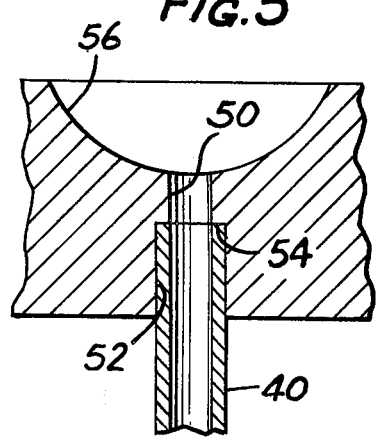

Turning to an important aspect of the present invention and referring to FIG. 3 which is a cross section taken generally along the line 3—3 in FIG. 2, the plate assembly 18 comprises a manifold plate 42, a collector plate 44 into which the collector tubes 40 are secured and an intermediate plate 46 which is located between the manifold plate and the collector plate. A flexible diaphragm 48 is positioned between the intermediate and collector plates for reasons which will be hereinafter described. Referring also to FIG. 5, the collector plate 44 has a plurality of openings 50 extending therethrough, with the underside portions 52 of the openings being of increased diameter and terminating in an annular shoulder 54. The collector tubes 40 have an outside diameter that is slightly greater i.e., a few thousandths of an inch that the inside diameter of the enlarged portion 54 so that when they are inserted therein, they are compressed slightly to provide a snug, secure fit. Moreover, the inside diameter of the collector tubes 40 is preferably approximately equal to the diameter of the openings 50 adjacent thereto as shown in FIG. 5. Near the upper side of the collector plate 44, the openings 50 are enlarged into a generally smooth, preferably hemispherical shaped portion 56, as shown in FIGS. 4 and 5. The size of the enlarged portion 56 is preferably predetermined so that when the diaphragm is displaced into contact with the surface of the hemispherical portion 56, the volume displaced is of a precise predetermined amount.

The intermediate plate 46 also has a plurality of openings 58 that are coextensive with the openings 50 and which also have an enlarged portion 60 that is preferably similarly hemispherically shaped and of predetermined size. The manifold plate 42 has a large recessed portion 62 in the lower side thereof which is coextensive with all of the openings 58 in the intermediate plate. An aperture 64 communicates the portion 62 with a connector nozzle 66 (see FIG. 1) to which the flexible conduit or tubing 28 is attached. Thus, positive or negative pressure that is present within the tubing 28 is communicated to the recessed portion 62 through the aperture 64. Since the openings 58 in the intermediate plate are in communication with the recessed portion 62 of the manifold plate, the positive and negative pressure is applied to the flexible diaphragm 48 during operation. A seal 68 may be provided around the periphery of the recessed portion between the intermediate and manifold plates to prevent leakage.

To transfer samples from receptacle to a plurality of culture wells, the receptacle having the culture material therein is placed below the plate assembly 18 on the base 12 and the switch 32 is placed in the position whereby positive pressure is applied through the nozzle 38 and flexible conduit 28 so that the positive pressure deflects the diaphragm 48 downwardly into the hemispherical portions 56. The knob 24 is then rotated so that the assembly 18 is lowered to immerse the ends of the tubes 40 into the liquid in the wells having the culture material therein. The switch 32 is then moved to the position whereby vacuum is communicated to the common conduit 28 and the diaphragm 48 is deflected upwardly into contact with the walls of the enlarged portion 60 of the intermediate plate. By moving the impervious diaphragm 48 from the lower to the upper position, the liquid is suctioned upwardly into the collector tubes 40. To transfer the liquid from the collector tubes to another device, the knob 24 is rotated to raise the assembly 18 so that another tray can be placed beneath the collector tubes and the assembly can then be manipulated to the proper elevation whereupon the switch 32 can then be moved to apply positive pressure to thereby force the liquid from the tubes to the desired locations.

In keeping with the present invention, while the manifold plate 42 is preferably securely attached to the cross support 20, the intermediate and collector plates are preferably releasably secured to the manifold plate. To hold the plates together, four threaded screws 70 are positioned at the four corner portions of the manifold plate outside of the outer periphery of the recessed portion 62. The threaded screws 70 pass through larger diameter, non-interfering apertures 72 in the manifold and intermediate plates, respectively, and engage a threaded aperture in the collector plate. By tightening the screws 70, the collector plate will be drawn upwardly so as to compress the diaphragm 48 in sealing engagement and to tighten the manifold, intermediate, and collector plates together. Conversely, by loosening the screws 70, the collector plate with the tubes secured thereto can be removed for cleaning and the intermediate plates 46 can also be removed for similar reasons.

In accordance with an important aspect of the present invention, the size of the enlarged portions 56 and 60 determine the volume that is extracted by the pipetting apparatus and, if the volume traversed by the diaphragm in each of the hemispherical portions 56 and 60 of the plates is 50 microliters, for example, the application of positive and negative pressure in the manner as previously described will extract a sample volume of about 100 microliters. In the event that some precise quantity other than 100 microliters is desired to be extracted, a separate intermediate plate 46 having hemispherical portions 60 which are of some other volume than the 50 microliters, i.e., about 25 microliters, for example, may be substituted. Thus, by going through the operating steps previously described, a total of 75 microliters may be extracted, since the movement of the diaphragm from the lower opening 56 to the rest position shown in FIG. 3 would effectively suction 50 microliters and the movement to the upper surface of the hemispherical portion 60 would suction an additional 25 microliters. It should also be understood that 25 microliters may be extracted by merely inserting the tubes in the well containing the cultures to be sampled without applying positive pressure to deflect the membrane downwardly. In other words, the application of vacuum pressure would merely move the diaphragm 48 from the position shown in FIG. 3 upwardly into contact with the hemispherical portions 60 which would effectively suction only 25 microliters.

As is shown in FIG. 4, the matrix or array of openings 58 in the intermediate plate 46 form a rectilinear matrix or array which comprises 12 rows, each of which have a total of 8 openings for a total of 96 places or locations. Since the cultural trays in which the sample cultures are developed are becoming increasingly standardized, it is preferred that the size of the matrix or array of collector tubes be compatible with the location of the individual culture wells in such trays. Thus, it is preferred that the array of collector tubes 40 fit within the dimensions of about 2.5 to about 4 inches. Thus, the adjacent openings 58 will be spaced apart approximately 0.355 inches from center to center. The enlarged portions 56 of the collector plate as previously mentioned, are preferably hemispherical in shape and may have the dimensions of about 0.125 inches in depth with a radius of about 0.1875 inches. With such dimensions, adjacent enlarged portions 56 do not merge with one another as is desired.

It should also be understood that the sources of vacuum and positive pressure are typically present in most laboratories and the apparatus embodying the present invention is compatible with typical laboratory vacuum and positive pressures of about 15 pounds per square inch so that flexible tubing can be used for interconnecting the nozzles 36 and 38 with the laboratory supplies.

The use of the snug fitting of the collector tubes 40 into the increased diameter lower portion 52 of the openings 50 which terminates in the annular shelf 52 has a quality control advantage during fabrication in that the tubes can be inserted to a uniform depth since the ends of the tubes cannot penetrate inwardly beyond the annular shelf 54 and therefore cannot penetrate into the hemispherical portion 56. If the ends of the tubes could enter the portion 56, they could cut the diaphragm when it is deflected downwardly upon application of positive pressure. Thus, the use of the annular shelf prevents the ends of the inserted collector tubes from cutting the diaphragm and also provides a reliable and uniform depth of insertion of the tubes within the collector plate during fabrication.

While various embodiments of the present invention have been shown and described, various modifications, substitutions and alternatives will be suggested to those skilled in the art. Accordingly, the scope of the protection to be afforded this invention should not be limited by the particular embodiments shown and described, but should be determined in terms of the definitions of the invention as set forth in the appended claims and equivalents thereof.

What is claimed is:

1. Apparatus for pipetting a plurality of predetermined quantities of a liquid, comprising:

a collector plate having a plurality of openings, the lower portion of the collector plate being adapted to receive a plurality of elongated hollow collector tubes in said openings, said opening communicating the lower surface with the upper surface, each of said openings in said upper surface having an enlarged generally smooth portion of a first predetermined volume;

a manifold plate having a recess in the lower surface thereof and an aperture communicating said recess with the opposite side thereof, said recess communicating fluid pressure from said aperture to said recess;

an intermediate plate located between said manifold plate and said collector plate and having openings generally coextensive with the openings in said collector plate, said openings communicating with said recess of said manifold plate, each of the openings having an enlarged generally smooth portion on the side adjacent said collector plate, each of said enlarged portions having a second predetermined volume;

a flexible impervious diaphragm positioned between said intermediate plate and said collector plate and adapted to be deflected upwardly or downwardly within each of said enlarged portions of said openings of said intermediate plate and collector plate, respectively, in response to selective application of fluid pressure thereto;

a plurality of elongated hollow collector tubes secured to the lower side of said collector plate within said openings;

means for connecting said manifold plate aperture to sources of positive and negative fluid pressure for deflecting said flexible diaphragm in opposite directions, respectively; and, frame means for supporting said plates, said frame means being connected to at least one of said plates.

2. Apparatus as defined in claim 1 wherein said second predetermined volume is approximately 50 microliters.

3. Apparatus as defined in claim 1 wherein the lower portion of said openings in said collector plate have an increased diameter terminating in an annular shelf, the ends of said collector tubes abutting said annular shelf.

4. Apparatus as defined in claim 3 wherein the inside diameter of said tubes is approximately equal to the outside diameter of said opening adjacent said annular shelf.

5. Apparatus as defined in claim 1 wherein said enlarged openings are generally hemispherical in form.

6. Apparatus as defined in claim 1 wherein an alternate intermediate plate having said enlarged portions with a third predetermined volume can be substituted for the initial intermediate plate having said second predetermined volumes.

7. Apparatus as defined in claim 6 wherein said third predetermined volume is approximately 25 micrometers.

8. Apparatus as defined in claim 1 wherein said frame means includes a vertical member and a vertically adjustable cross member operably associated therewith, said manifold plate being attached to said cross member so that all of said plates are vertically adjustable.

9. Apparatus as defined in claim 8 including releasable attachment means for releasably attaching said manifold, intermediate and collector plates together.

10. Apparatus as defined in claim 9 wherein said attachment means comprises one or more threaded screws engaging a threaded aperture in one of said plates to thereby hold said plates together.

11. Apparatus as defined in claim 1 wherein said means for connecting said sources of positive and negative pressure comprises a flexible conduit having one end attached to said manifold aperture, the opposite end thereof being connected to valve means for communicating said flexible conduit to the source of positive pressure when in a first position and to the source of vacuum pressure when in a second position.

12. Apparatus as defined in claim 11 wherein said valve means comprises an electrically actuated solenoid valve.

13. Apparatus as defined in claim 8 wherein said vertical member and vertically adjustable cross member are interconnected by a rack and pinion gear arrangement having a rotatable knob for adjusting the elevation of said plates and collector tubes.

14. Apparatus as defined in claim 1 wherein said openings in said collector plate are arranged in a rectilinear array.

15. Apparatus as defined in claim 14 wherein said rectilinear array comprises 8 parallel rows, each row having 12 openings.

16. Apparatus as defined in claim 1 wherein said diaphragm comprises rubber.

* * * * *